US010285967B2

(12) United States Patent
Cruz-Hernandez et al.

(10) Patent No.: US 10,285,967 B2
(45) Date of Patent: *May 14, 2019

(54) MONOACYLGLYCEROLS FOR USE IN CONJUNCTION WITH A LIPASE INHIBITOR AND/OR DIETS LOW IN FAT AND/OR CALORIES

(71) Applicant: NESTEC S.A., Vevey (CH)

(72) Inventors: Cristina Cruz-Hernandez, Epalinges (CH); Claudia Roessle, Morges (CH); Lada Frolova, Morges (CH)

(73) Assignee: Nestec S.A., Vevey (CH)

(*) Notice: Subject to any disclaimer, the term of this patent is extended or adjusted under 35 U.S.C. 154(b) by 0 days.

This patent is subject to a terminal disclaimer.

(21) Appl. No.: 15/952,504

(22) Filed: Apr. 13, 2018

(65) Prior Publication Data

US 2018/0228759 A1  Aug. 16, 2018

Related U.S. Application Data

(63) Continuation of application No. 15/032,895, filed as application No. PCT/EP2014/073024 on Oct. 27, 2014, now Pat. No. 9,980,934.

(60) Provisional application No. 61/896,530, filed on Oct. 28, 2013.

(51) Int. Cl.
| | | |
|---|---|---|
| A61K 31/232 | (2006.01) | |
| A61K 31/365 | (2006.01) | |
| A61K 31/337 | (2006.01) | |
| A61K 45/06 | (2006.01) | |
| A23L 33/00 | (2016.01) | |
| A23L 33/15 | (2016.01) | |
| A23L 33/155 | (2016.01) | |

(52) U.S. Cl.
CPC ............ *A61K 31/232* (2013.01); *A23L 33/15* (2016.08); *A23L 33/155* (2016.08); *A23L 33/30* (2016.08); *A61K 31/337* (2013.01); *A61K 31/365* (2013.01); *A61K 45/06* (2013.01); *A23V 2002/00* (2013.01)

(58) Field of Classification Search
None
See application file for complete search history.

(56) References Cited

U.S. PATENT DOCUMENTS

| 9,000,039 B2 | 4/2015 | Destaillats et al. |
| 2016/0263072 A1 | 9/2016 | Roessle et al. |
| 2016/0263073 A1 | 9/2016 | Roessle et al. |

FOREIGN PATENT DOCUMENTS

| EP | 0465423 | 1/1992 |
| EP | 2508180 | 10/2012 |
| WO | 0119378 | 3/2001 |

OTHER PUBLICATIONS

Reeves, P. J. Nutr. 1997, vol. 127 pp. 838S-841S.*
Cruz-Hernandez, C. el al., Nutrients 2012, vol. 4, pp. 1781-1793.*
Cruz-Hernandez et al. "Benefits of Structured and Free Monoacylglycerols to Deliver Eicosapentaenoic (EPA) in a Model of Lipid Malabsorption" Nutrients, 2012, vol. 4, pp. 1781-1793.
Cruz-Hernandez et al. "Lipase inhibitor orlistat decreases incorporation of eicosapentaenoic and docosahexaenoic acids in rat tissues" Nutrition Research, 2010, vol. 30, pp. 134-140.
Article entitled "Comparison of MAG and Fish Oil Efficacy", ClinicalTrials.gov, 2013, 4 pages.
Cruz-Hernandez et al. "PP077-SUN: Comparison of the Efficacy of MAG and TAG to Deliver LC-PUFA Under Malabsorption Conditions" Clinical Nutrition, 2014, vol. 33, p. S48.
Cruz-Hernandez, C. et al., Nutrients 2012 vol. 4, pp. 1781-1793.
Reeve, P. J. Nutr. 1997 vol. 127 pp. 838S-841S.
Nagao et al., "Effects of Fats and Oils on the Bioaccessibility of Carotenoids and Vitamin E in Vegetables", Bioscience Biotechnology Biochemistry, 2013, vol. 77, No. 5, pp. 1055-1060.
Finer et al., "One-year treatment of obesity: a randomized, double-blind, placebo-controlled, multicentre study of orlistat, a gastrointestinal lipase inhibitor", International Journal of Obesity Related Metabolic Disorder, Mar. 2000, vol. 24, No. 3, pp. 306-313.

* cited by examiner

*Primary Examiner* — Heidi Reese
(74) *Attorney, Agent, or Firm* — K&L Gates LLP (57) ABSTRACT

In an embodiment, compositions comprising monoacylglycerols (MAG), such as sn-1 MAG, are administered with a lipase inhibitor, such as tetrahydrolipstatin, and/or with a diet low in fat and/or calories. In another embodiment, compositions comprising MAG, such as sn-1 MAG, are administered concurrently with a lipase inhibitor, such as tetrahydrolipstatin, and/or with fat-soluble nutrients. The compositions and the methods of using the compositions enhance absorption of fatty acids and fat-soluble nutrients such as fat-soluble vitamins and carotenoids to address nutritional deficiencies due to a weight loss diet used in association with a lipase inhibitor.

16 Claims, 6 Drawing Sheets

MONOACYLGLYCEROLS FOR USE IN CONJUNCTION WITH A LIPASE INHIBITOR AND/OR DIETS LOW IN FAT AND/OR CALORIES

PRIORITY CLAIM

This application is a continuation of U.S. application Ser. No. 15/032,895 filed Apr. 28, 2016, which is a National Stage of International Application No. PCT/EP14/73024 filed Oct. 27, 2014, which claims priority to U.S. Provisional Patent Application No. 61/896,530 filed Oct. 28, 2013, the entire contents of which are incorporated herein by reference.

BACKGROUND

The present disclosure generally relates to health and nutrition. More specifically, the present disclosure relates to nutritional compositions that can promote absorption of fatty acids and fat-soluble nutrients.

Gastric and pancreatic lipase inhibitors such as tetrahydrolipstatin (commercially available as XENICAL® and ALLI®) can be used as anti-obesity drugs because these compounds prevent fats from being hydrolyzed and absorbed, thus decreasing calorie intake. Specifically, tetrahydrolipstatin binds covalently to the active site of such lipases to block lipid hydrolysis.

In conjunction with changes in diet and lifestyle, a lipase inhibitor has a higher efficacy than changes in diet and lifestyle alone. Finer et al., Int. J. Obes. Relat. Metab. Disord., 24(3):306-13 (March 2000). However, common side effects can include gastrointestinal problems, such as oily stools; deficiencies in fat-soluble nutrients, including vitamins A, D, E, K and beta-carotene; and liver or kidney damage.

Decreased lipid absorption can result in reduced absorption of long-chain polyunsaturated fatty acids (LC-PUFAs). LC-PUFAs are important fatty acids obtained from the diet and needed for normal body function. Two critical LC-PUFAs, eicosapentaenoic acid (EPA) and docosahexaenoic acid (DHA), are obtained from conversion of alpha-linolenic acid (ALA) in the body, but this conversion occurs at a very low rate; thus supplementation of EPA and DHA is highly recommended. Therefore, the low LC-PUFA levels resulting from decreased lipid absorption associated with lipase inhibitors or low fat diets can increase the risk of cardiovascular and metabolic diseases, especially in cases where n-3 LC-PUFAs such as EPA and DHA are minimally absorbed.

Reduced absorption of fat-soluble nutrients, such as vitamins A, D, E and K and carotenoids such as beta-carotene and lutein, can also result from decreased lipid absorption. The resultant low levels of these vitamins and carotenoids can elevate the risks of a variety of conditions, such as cardiovascular diseases, coagulation disorders, impaired wound healing and immune function, and bone and muscle function disorders.

SUMMARY

The present disclosure provides compositions comprising monoacylglycerols (MAG), such as sn-1(3) MAG, for administration with a lipase inhibitor, such as tetrahydrolipstatin, and/or with a diet low in fat and/or calories. In sn-1(3) MAG, the sn-1 or sn-3 position is occupied by an acyl group, such as a fatty acid, and the sn-2 position is not occupied by a fatty acid.

Accordingly, in a general embodiment, the present disclosure provides a method that includes administering a therapeutically effective amount of monoacylglycerols to an individual that has a characteristic selected from the group consisting of periodic consumption of a lipase inhibitor, a diet low in fat, a diet low in calories, and combinations thereof.

In an embodiment, the monoacylglycerols comprise a therapeutically effective amount of sn-1(3) monoacylglycerols.

In an embodiment, the amount of monoacylglycerols is therapeutically effective to promote absorption of fatty acids and enhance delivery of fat-soluble nutrients in the individual.

In an embodiment, the lipase inhibitor is tetrahydrolipstatin.

In an embodiment, the monoacylglycerols comprise a functional fatty acid.

In an embodiment, the method includes administering a fat-soluble nutrient to the individual. The fat-soluble nutrient can be selected from the group consisting of fat-soluble vitamins and carotenoids.

In an embodiment, the method includes administering the monoacylglycerols daily for at least three weeks.

In an embodiment, the monoacylglycerols include at least one of MAG-DHA, MAG-EPA or MAG-ARA.

In an embodiment a method is provided for treating a nutrient deficiency in an individual that has a characteristic selected from the group consisting of periodic consumption of a lipase inhibitor, a diet low in fat, a diet low in calories, and combinations thereof, comprising administering to an individual in need thereof a therapeutically effective amount of a composition comprising monoacylglycerols, and a fat-soluble nutrient, wherein the acyl group of the monoacylglycerols is selected from the group consisting of polyunsaturated fatty acids.

In another embodiment, a kit is provided. The kit includes: a first composition comprising monoacylglycerols; a second composition comprising a lipase inhibitor; and a third composition that is a nutritional composition that provides complete nutrition.

In an embodiment, the nutritional composition is designed such that a predetermined number of servings of the nutritional composition per day provide a diet low in at least one of fat or calories.

In another embodiment, a kit is provided. The kit includes: a first composition comprising monoacylglycerols; a second composition comprising a lipase inhibitor; and a third composition that comprises fat-soluble nutrients.

In an embodiment, the fat-soluble nutrients are selected from the group consisting of vitamin A, isoforms of vitamin A, vitamin D, isoforms of vitamin D, vitamin E, isoforms of vitamin E, vitamin K, isoforms of vitamin K, beta-carotene, lutein, and combinations thereof.

In another embodiment, a composition is provided. The composition includes a lipase inhibitor and sn-1(3) monoacylglycerols.

In an embodiment, the lipase inhibitor is tetrahydrolipstatin.

In an embodiment, the composition further includes fat-soluble nutrients.

In an embodiment, the sn-1(3) monoacylglycerols include at least one of MAG-DHA, MAG-EPA or MAG-ARA.

In an embodiment, no more than 25 weight %, preferably no more than 15 weight %, of the total monoacylglycerols are Sn-2 monoacylglycerols.

An advantage of the present disclosure is to address side effects of lipase inhibitors, such as tetrahydrolipstatin, and/or diets low in fat and/or calories.

A further advantage of the present disclosure is to provide a food composition that enables the efficient uptake of fatty acids despite conditions of lipid malabsorption, such as lipase inhibitor administration and diets low in calories and/or fat.

Another advantage of the present disclosure is to provide an optimal glyceride structure for substantial uptake of fatty acids despite conditions of lipid malabsorption, such as lipase inhibitor administration and diets low in calories and/or fat.

Still another advantage of the present disclosure is to enhance absorption of anti-inflammatory fatty acids despite conditions of lipid malabsorption, such as lipase inhibitor administration and diets low in calories and/or fat.

An additional advantage of the present disclosure is to provide fatty acids in a form that do not need to be hydrolyzed prior to absorption.

Another advantage of the present disclosure is to enhance absorption of fat-soluble nutrients despite conditions of lipid malabsorption, such as lipase inhibitor administration and diets low in calories and/or fat.

Still another advantage of the present disclosure is to provide fatty acids and enhance absorption of fat-soluble nutrients with compounds that have intrinsic emulsifying properties.

Yet another advantage of the present disclosure is to provide fatty acids and fat-soluble nutrients in a way that is compatible with a diet low in calories and/or fat.

An additional advantage of the present disclosure is to provide fatty acids and fat-soluble nutrients in way that is well tolerated, without aggravating any steatorrhea.

Another advantage of the present disclosure is to correct nutritional deficiencies in LC-PUFAs and fat-soluble nutrients due to a weight loss diet used in association with a lipase inhibitor.

Still another advantage of the present disclosure is to additionally provide preventive benefits with respect to cardiovascular and metabolic disease.

Yet another advantage of the present disclosure is to provide kits that enable a consumer to easily consume each component of the diet plan.

Additional features and advantages are described herein, and will be apparent from, the following Detailed Description and the Figures.

DETAILED DESCRIPTION

All percentages expressed herein are by weight of the total weight of the composition unless expressed otherwise. When reference is made to the pH, values correspond to pH measured at 25° C. with standard equipment. As used in this disclosure and the appended claims, the singular forms "a," "an" and "the" include plural referents unless the context clearly dictates otherwise. As used herein, "about" is understood to refer to numbers in a range of numerals. Moreover, all numerical ranges herein should be understood to include all integers, whole or fractions, within the range. The composition disclosed herein may lack any element that is not specifically disclosed herein. Thus, the disclosure of an embodiment using the term "comprising" includes a disclosure of an embodiment "consisting essentially of" and an embodiment "consisting of" the referenced components. Any embodiment disclosed herein can be combined with any other embodiment disclosed herein.

"Overweight" is defined for a human as a body mass index (BMI) between 25 and 30. "Obese" is defined for a human as a BMI greater than 30. BMI is defined as the value resulting from the division equation in which the numerator is the weight in kilograms and the denominator is the height in meters, squared.

"Prevention" includes reduction of risk and/or severity of a condition or disorder. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measures. The terms "treatment," "treat" and "alleviate" are further intended to include the dietary management of a disease or condition or the dietary management for prophylaxis or prevention a disease or condition. A treatment can be patient- or doctor-related.

As used herein, a "therapeutically effective amount" is an amount that prevents a deficiency, treats a disease or medical condition in an individual or, more generally, reduces symptoms, manages progression of the diseases or provides a nutritional, physiological, or medical benefit to the individual. The therapeutically effective amount that is required to achieve a therapeutic effect will, of course, vary with the particular composition, the route of administration, the age and the condition of the recipient, and the particular disorder or disease being treated.

"Animal" includes, but is not limited to, mammals, which includes but is not limited to, rodents, aquatic mammals, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage. As used herein, the term "patient" is understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human, having or at risk for a medical condition that can benefit from the treatment.

"Food product" and "food composition," as used herein, are understood to include any number of optional additional ingredients, including conventional food additives, for example one or more proteins, carbohydrates, fats, acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers and/or vitamins. The optional ingredients can be added in any suitable amount.

As used herein, "complete nutrition" includes nutritional products and compositions that contain sufficient types and levels of macronutrients (protein, fats and carbohydrates) and micronutrients to be sufficient to be a sole source of nutrition for the animal to which the composition is administered. Patients can receive 100% of their nutritional requirements from such complete nutritional compositions. As used herein, "incomplete nutrition" includes nutritional products or compositions that do not contain sufficient levels of macronutrients (protein, fats and carbohydrates) or micronutrients to be sufficient to be a sole source of nutrition for the animal to which the composition is administered. Partial or incomplete nutritional compositions can be used as a nutritional supplement.

A "kit" means that the components of the kit are physically associated in or with one or more containers and considered a unit for manufacture, distribution, sale, or use. Containers include, but are not limited to, bags, boxes, cartons, bottles, packages of any type or design or material, over-wrap, shrink-wrap, affixed components (e.g., stapled, adhered, or the like), or combinations thereof.

"Concurrent" and "concurrently" in the context of the present disclosure mean in the same day, preferably in the same twelve hour period, more preferably within the same hour, most preferably simultaneously.

A "diet low in fat and/or calories" is a diet in which 1,000 calories/day or less and/or 150 g of calories from fat/day or less are consumed. In such a diet, preferably 800 calories/day or less are consumed and preferably 125 g of calories from fat/day or less are consumed.

Figure 1:
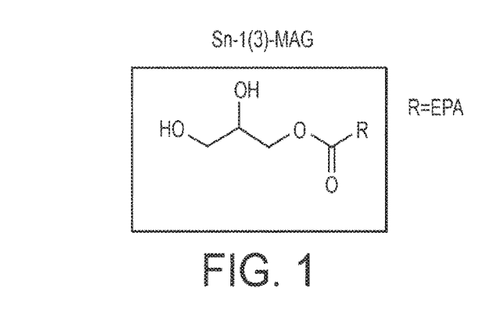
FIG. 1 shows the chemical structure of a sn-1(3) MAG. R is a fatty acid.

The present disclosure provides compositions comprising monoacylglycerols (MAG), such as sn-1(3) MAG. FIG. 1 depicts the chemical structure of a sn-1(3) MAG, and R is the fatty acid. For example, 1,3 MAG-EPA is the chemical structure shown in FIG. 1 in which R is EPA. The sn-1(3) MAG may be chemically synthesized, for example using glycerol and fish oil. The composition can comprise the sn-1(3) MAG in an amount corresponding to 1% to 40% of the energy of the composition, preferably from 5% to 40% of the energy of the composition.

Preferably the compositions comprise MAG in an amount that is therapeutically effective for providing fatty acids and/or enhancing absorption of fat-soluble nutrients. More preferably the compositions comprise sn-1(3) MAG in an amount that is therapeutically effective for providing fatty acids and/or enhancing absorption of fat-soluble nutrients.

Figure 7:
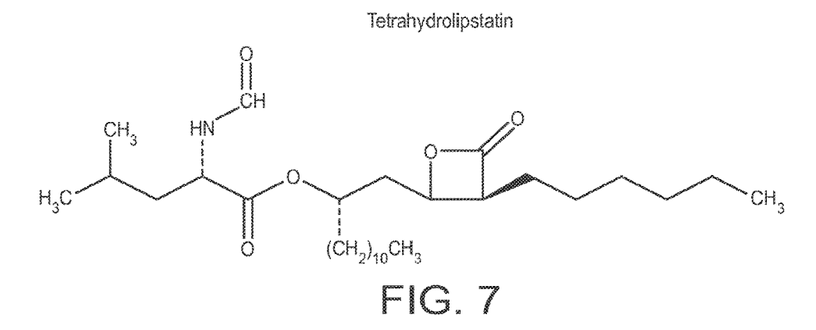
FIG. 7 shows the chemical structure of tetrahydrolipstatin.

The present disclosure also provides methods in which such compositions are administered concurrently with a lipase inhibitor, such as tetrahydrolipstatin (FIG. 7), and/or with a diet low in fat and/or calories. Preferably, the individual is consuming the lipase inhibitor periodically, such as weekly or daily. Preferably, compositions comprising a therapeutically effective amount of monoacylglycerols (MAG), such as sn-1(3) MAG, are administered daily and concurrently with a lipase inhibitor and/or with a diet low in fat and/or calories for at least three weeks, more preferably at least eight weeks, and most preferably at least twelve weeks. A non-limiting example of a diet low in fat and calories is a diet that solely uses liquid products designed to restrict caloric intake, while providing complete nutrition, such as the full meal replacement liquid products of Nestle S.A.'s OPTIFAST®. For example, a diet low in fat and calories may be a diet in which five servings of a composition are consumed daily, and each serving has about 160 calories, about 25 calories from fat, about 20 g of carbohydrates, and about 14 g of protein.

The present disclosure also provides methods in which compositions comprising MAG are administered concurrently with a lipase inhibitor, such as tetrahydrolipstatin (FIG. 2), and/or with fat-soluble nutrients. Non-limiting examples of fat-soluble nutrients include fat-soluble vitamins, such as vitamins A, D, E and K and their isoforms, and carotenoids, such as beta-carotene and lutein. Preferably, the individual is consuming the lipase inhibitor periodically, such as weekly or daily. Preferably, the compositions comprising monoacylglycerols (MAG), such as sn-1(3) MAG, are administered daily and concurrently with the lipase inhibitor and/or with fat-soluble nutrients for at least three weeks, more preferably at least eight weeks, and most preferably at least twelve weeks.

Sn-1(3) MAG interacts with vitamins due to its emulsifying properties and thus facilitates absorption of vitamins A, D, E and K, potentially synergistically. Therefore the compositions according to the present disclosure can correct nutritional deficiencies in vitamins and fatty acids (PUFA), for example nutritional deficiencies in vitamins and fatty acids (PUFA) related to low fat diets. Preferably the lipase inhibitor is administered in an amount that is therapeutically effective to decrease the gastrointestinal absorption of fats.

According to the present disclosure, concurrent administration of the lipase inhibitor and the composition comprising MAG includes administration of the lipase inhibitor separately from the composition comprising monoacylglycerols and also includes administration of the lipase inhibitor and the MAG in the same composition. Similarly, concurrent administration of the lipase inhibitor and the diet low in fat and/or calories includes administration of the lipase inhibitor separately from a serving of the diet low in fat and/or calories and also includes administration of the lipase inhibitor and a serving of the diet low in fat and/or calories in the same composition. Also similarly, concurrent administration of the lipase inhibitor and the fat-soluble nutrients includes administration of the lipase inhibitor separately from a serving of the fat-soluble nutrients and also includes administration of the lipase inhibitor and a serving of the fat-soluble nutrients in the same composition.

The recipient of administration may be any individual but preferably is an overweight or obese individual or an individual at risk of overweight or obesity. The compositions comprising MAG can be implemented in a method of treating or preventing overweight or obesity. In some embodiments, the compositions comprising MAG can provide n-3 LC-PUFAs in an amount that is therapeutically effective to treat or prevent cardiovascular disease or rheumatoid arthritis; increase the level of eicosanoids such as prostaglandin-3; enhance brain and retina development; treat or prevent vision decline; and/or enhance immune function.

The acyl group of the MAG may be a functional fatty acid. A functional fatty acid is a fatty acid that provides a health benefit to an individual administered the fatty acid. Non-limiting examples of functional fatty acids include eicosapentaenoic acid (EPA), docosahexaenoic acid (DHA), α-linolenic acid (ALA), stearidonic acid (SA), γ-linolenic acid (GLA), dihomo-γ-linolenic acid (DGLA), docosapentanenoic acid (DPA), sciadonic acid, and juniperonic acid. Sciadonic acid is 5Z,11Z,14Z-eicosatrienoic acid. Juniperonic acid is 5(Z), 11(Z), 14(Z), 17(Z)-eicosatetraenoic acid.

Non-limiting examples of MAG that may be used in the compositions provided by the present disclosure include:

sn-1(3)-monoeicosapentaenoylglycerol
sn-1 (3)-monodocosahexaenoylglycerol
sn-1(3)-monooctadecatrienoylglycerol
sn-1(3)-monooctadecatetraenoylglycerol
sn-1(3)-monoeicosatrienoylglycerol
sn-1(3)-monodocosapentacnoylglycerol
sn-1(3)-monosciadonylglycerol
sn-1(3)-monojuniperonylglycerol
and combinations thereof.

Of course, the composition may comprise a mixture of different MAG with different fatty acids in the sn-1(3) position. The fatty acids may be mixed to achieve a particular ratio between n-3 and n-6 fatty acids. Non-limiting examples of suitable n-3 fatty acids include a-linolenic acid, stearidonic acid, eicosatrienoic acid, n-3 eicosatetraenoic acid, eicosapentaenoic acid, clupanodonic acid, docosahexaenoic acid, n-3 tetracosapentaenoic acid, and n-3 tetracosahexaenoic acid. Non-limiting examples of suitable n-6 fatty acids include linoleic acid, γ-linolenic acid, n-6 eicosadienoic acid, dihomo-γ-linolenic acid, arachidonic acid, n-6 docosadienoic acid, adrenic acid, n-6 docosapentaenoic acid, and calendic acid.

In an embodiment, the composition contains a combination of different sn-1(3) MAG such that the ratio of n-3 to n-6 fatty acids is about 5:1 to about 15:1, preferably about 8:1 to about 10:1.

Optionally, the composition contains sn-2 MAG in addition to the sn-1(3) MAG. Depending on the nature of the fatty acid used as acyl-group in the sn-1(3) position, such mixtures may form automatically through isomerisation. Therefore, an embodiment of the composition comprises 25% or less by weight of the total MAG as sn-2 MAG, preferably 15% or less by weight of the total MAG as sn-2 MAG. The sn-1 and sn-3 positions of the sn-2 MAG can be blocked by protective groups to limit isomerization. Non-limiting examples of suitable protective groups include acetyl groups, ethyl groups, propyl groups, vanillin, and other molecules able to form acetals. In some embodiments, the protective group bridges the hydroxyl groups in sn-1 and sn-3 positions.

Non-limiting examples of suitable sn-2 MAG include:
1,3-di acetyl-2-eicosapentaenoylglycerol
1,3-diethyl-2-eicosapentaenoylglycerol
1,3-dipropyl-2-eicosapentaenoylglycerol
a vanillin derivative of sn-2 mono eicosapentaenoylglycerol
other acetal derivatives of monoeicosapentaenoylglycerol and combinations thereof.

Unwanted isomerisation may be prevented or at least slowed significantly by adjusting the pH to the neutral range and/or by keeping the temperature of the composition low. Therefore, the composition may have a pH in the range of 5 to 8, preferably 5 to 7. The composition may be stored at 8° C. or below.

Isomerization of the MAG may further be prevented, even in the body after consumption, by inhibiting the action of lipase B. Therefore, the composition may comprise a lipase B inhibitor. Lipase B inhibitors are known to those of skill in the art. Edible lipase B inhibitors are preferred. "Edible" means that a material is approved for human or animal consumption.

The composition provided by the present disclosure may be any kind of edible composition. Preferably, the composition is a composition to be administered orally or enterally. For example, the composition may be selected from the group consisting of a food product, an animal food product, a pharmaceutical composition, a nutritional composition, a nutraceutical, a drink, a food additive, and a medicament. In an embodiment, the composition is a liquid nutritional formula to be administered enterally, e.g., in hospitals.

In an embodiment, the composition is a powdered composition to be reconstituted in milk or water. If the composition has the form of a powder, the powder may be a shelf stable powder. Shelf stability can be obtained, for example, by providing the composition with a water activity less than 0.2, for example in the range of 0.05 to 0.19, preferably in the range of 0.05 to 0.15. Water activity ($a_w$) is a measurement of the energy status of the water in a system and defined as the vapor pressure of water divided by that of pure water at the same temperature; therefore, pure distilled water has a water activity of exactly one.

The composition comprising MAG may be a nutritional composition that also contains a protein source and/or a carbohydrate source. Easily digestible carbohydrates and/or proteins are preferred. Proteins that are hydrolyzed at least partially are easier to digest and absorb. Therefore, the protein may have a degree of hydrolysis between 2 and 20%. If hydrolyzed proteins are required, the hydrolysis process may be carried out using any process known in the art. For example, a protein hydrolysate may be prepared by enzymatically hydrolysing a protein fraction in one or more steps. For an extensively hydrolysed protein, the proteins may be subjected to triple hydrolysis using Alcalase 2.4 L (EC 940459), then Neutrase 0.5 L (obtainable from Novo Nordisk Ferment AG) and then pancreatin at 55° C.

The nutritional composition may be a source of complete nutrition or may be a source of incomplete nutrition. As used herein, "complete nutrition" includes nutritional products and compositions that contain sufficient types and levels of macronutrients (protein, fats and carbohydrates) and micronutrients to be sufficient to be a sole source of nutrition for the animal to which the composition is administered. Individuals can receive 100% of their nutritional requirements from such complete nutritional compositions. As used herein, "incomplete nutrition" includes nutritional products or compositions that do not contain sufficient levels of macronutrients (protein, fats and carbohydrates) or micronutrients to be sufficient to be a sole source of nutrition for the animal to which the composition is administered. Partial or incomplete nutritional compositions can be used as a nutritional supplement.

In an embodiment, the diet low in fat and/or calories is achieved by consuming several compositions daily such that the compositions provided complete nutrition. The MAG may be provided by one or more of these compositions. As a non-limiting example, the diet low in fat and/or calories may be achieved by consuming five compositions daily, and each of the compositions can have 160 calories, 25 g of fat, sn-1(3) MAG, and optionally sn-2 MAG. The lipase inhibitor, such as tetrahydrolipstatin, may also be consumed daily and thus concurrently to such compositions as defined by the present disclosure.

To encourage concurrent administration, the composition comprising MAG, the servings of the diet low in fat and/or calories, and the lipase inhibitor may be provided in a kit. For example, each of the composition comprising MAG, the servings of the diet low in fat and/or calories, and the lipase inhibitor may be provided in separate containers in a single package. Similarly, the composition comprising MAG, the fat-soluble nutrients, and the lipase inhibitor may be provided in a kit. For example, each of the compositions comprising MAG, the fat-soluble nutrients, and the lipase inhibitor may be provided in separate containers in a single package.

EXAMPLES

The following non-limiting examples present scientific data developing and supporting the concept of administering sn-1(3) MAG to promote absorption of fatty acids and fat-soluble nutrients in a diet low in fat and/or calories in association with a lipase inhibitor.

Example 1

The concept was tested in a lipid maldigestion or malabsorption rat model. The maldigestion or malabsorption condition was obtained using XENICAL® (ORLISTAT), a pancreatic and gastric lipases inhibitor (tetrahydrolipstatin; see FIG. 7). Rats were fed during 21 days with long-chain polyunsaturated fatty acid (LC-PUFA) supplements containing mainly eicosapentaenoic (EPA) acid. Fish oil was used as a source of triacylglycerols, and different EPA glycerides were evaluated. XENICAL® (ORLISTAT) was given at a level sufficient to decrease lipid absorption by 40%. A group receiving fish oil without XENICAL® (ORLISTAT) was used as a positive control. At different time intervals (D3, D7, D14 and D21), the fatty acid profiles of red blood cell and plasma lipids were determined. At the end of the experiment, the fatty acid profiles of different tissues were determined.

The main objective was to follow the level of EPA in red blood cell and plasma lipids. The main comparison evaluated was the difference in EPA level between the group receiving EPA-containing sn-1(3) MAG (FIG. 1) in combination with XENICAL® (ORLISTAT) and the positive control group (fish oil+XENICAL® (ORLISTAT)).

Figure 2:
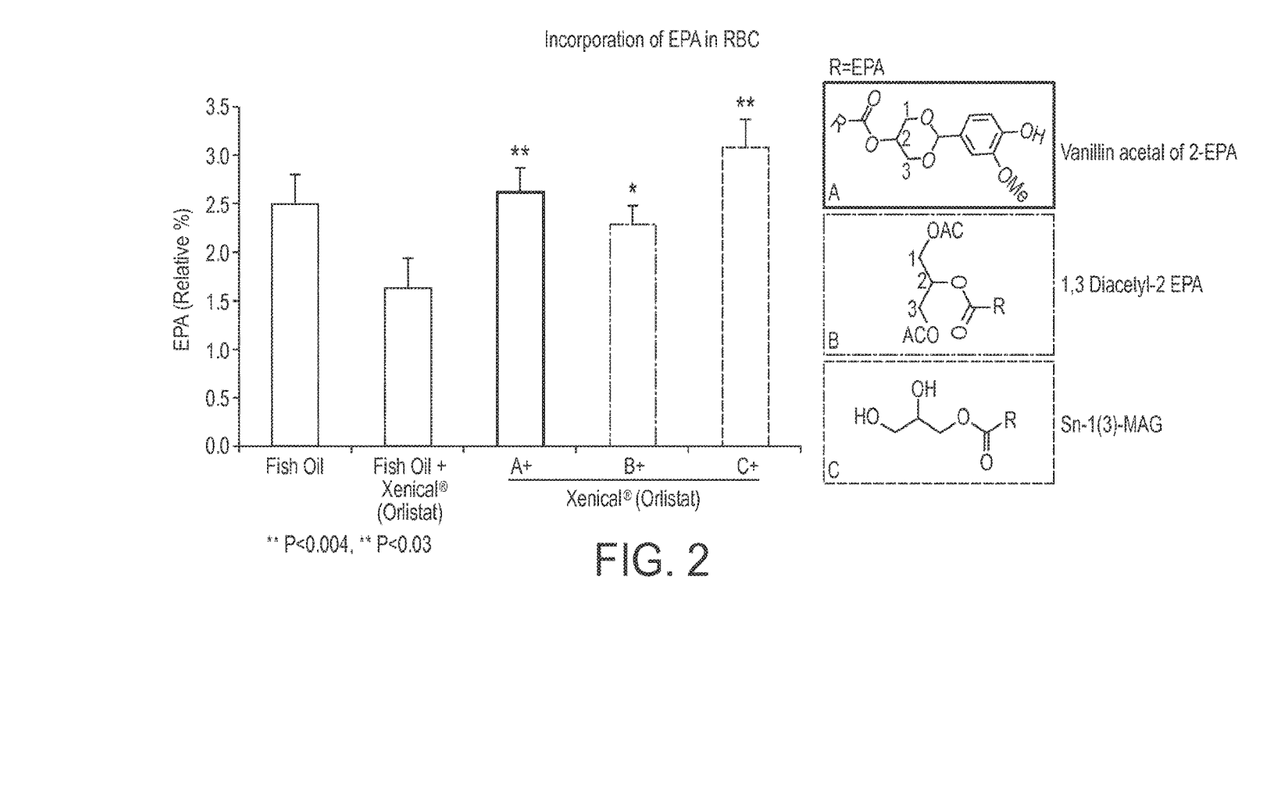
FIG. 2 depicts a graph showing the incorporation of EPA in red blood cells resulting from treatments of control rats fed fish oil with or without tetrahydrolipstatin and rats fed tetrahydrolipstatin and vanillin acetal of 2-EPA (Group A), 1,3 diacetyl-2 EPA (Group B), and 1,3 MAG-EPA (values are means±SEM, n=6).

As an example, data obtained for EPA levels in red blood cell lipids at day 7 are reported in FIG. 2. The statistical evaluation revealed that the use of XENICAL® (ORLISTAT) decreases EPA incorporation in red blood cells (comparison between the group receiving fish oil in combination with XENICAL® (ORLISTAT) and the group receiving fish oil without XENICAL® (ORLISTAT)). This comparison corroborates the validity of the model. The level of EPA incorporated in red blood cells in animals receiving the sn-1(3) MAG that contained EPA is statistically higher that the fish oil+group receiving fish oil in combination with XENICAL® (ORLISTAT) (all P values lower than 0.05), and more surprisingly, even higher than the fish oil group.

This example clearly demonstrates that in conditions of lipid maldigestion or malabsorption, the incorporation of LC-PUFAs provided as triacylglycerols is reduced. However, if LC-PUFAs are provided as sn-1(3) MAG (Group C), the incorporation in tissue is improved, even in conditions of lipid maldigestion or malabsorption.

Example 2

Figure 3:
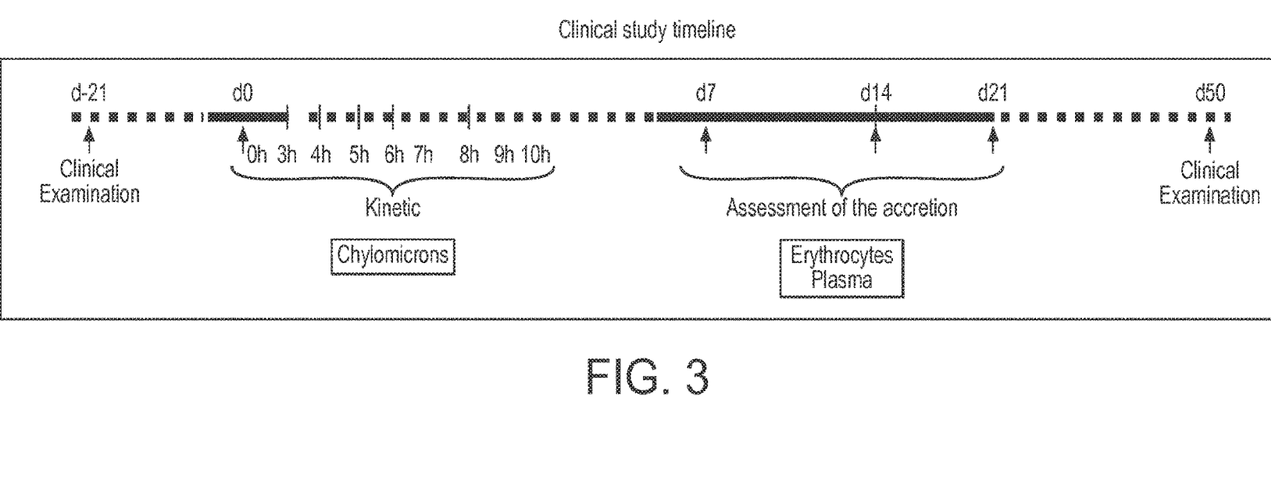
FIG. 3 shows the timeline of a clinical study supporting the concept of administering sn-1(3) MAG to promote absorption of fatty acids and fat-soluble nutrients in a diet low in fat and/or calories in association with a lipase inhibitor.

This clinical study compared the efficacy of sn-1(3) MAG and fish oil (TAG) in delivering EPA in humans under lipid maldigestion conditions induced by XENICAL® (ORLISTAT). The comparison was tested in volunteers having a BMI of 37-40 kg/m2 and treated with XENICAL® (ORLISTAT) to induce lipid maldigestion or not treated with XENICAL® (ORLISTAT). The primary objective was to assess accretion of EPA in erythrocytes over 21 days when consumed as fish oil (TAG) or sn-1(3) MAG. The secondary objectives were to assess accretion of EPA in plasma over 21 days and also to assess the pharmacokinetics of EPA after an acute dose either in the form of sn-1(3) MAG or TAG (AUC in chylomicrons over 10 hours postprandial). See FIG. 3.

TABLE 1

Experimental Groups

| Group No. | Oil Type and number per day | | Total EPA (mg) | Orlistat ® (120 mg) and number per day | |
|---|---|---|---|---|---|
| 1 (n = 11) | Fish oil | 3 | 504 | No | |
| 2 (n = 11) | MAG | 3 | 500 | No | |
| 3 (n = 11) | Fish oil | 3 | 504 | Yes | 3 |
| 4 (n = 11) | MAG | 3 | 500 | Yes | 3 |

Figure 4:
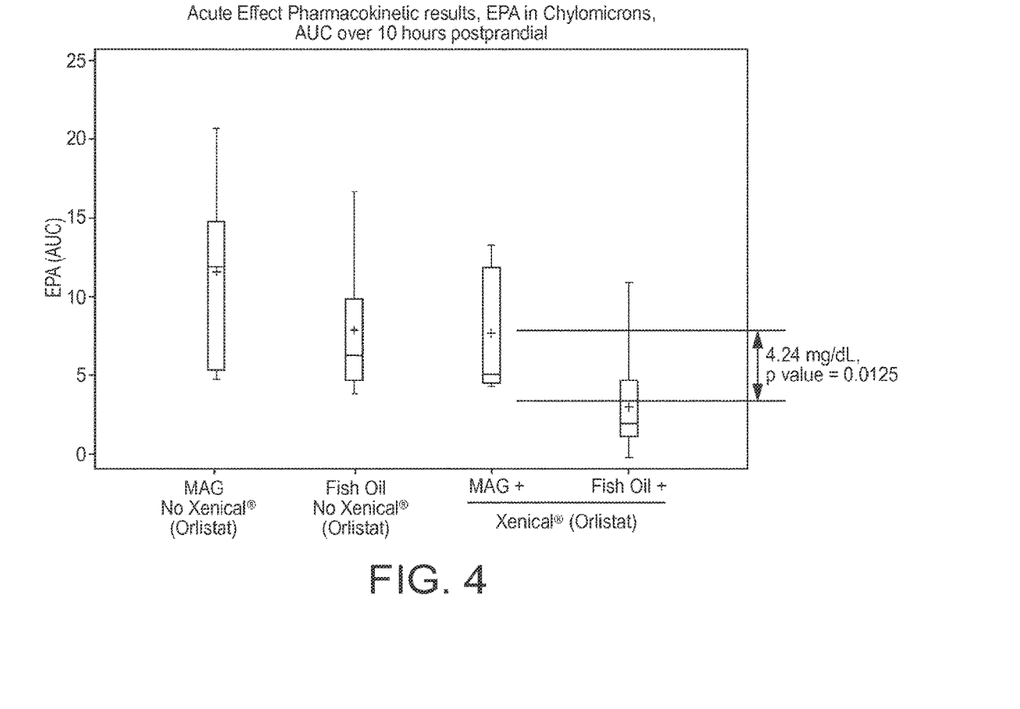
FIG. 4 shows acute effects in the clinical study, namely pharmacokinetic results as measured by EPA in chylomicrons, AUC over 10 hours postprandial.
Figure 5:
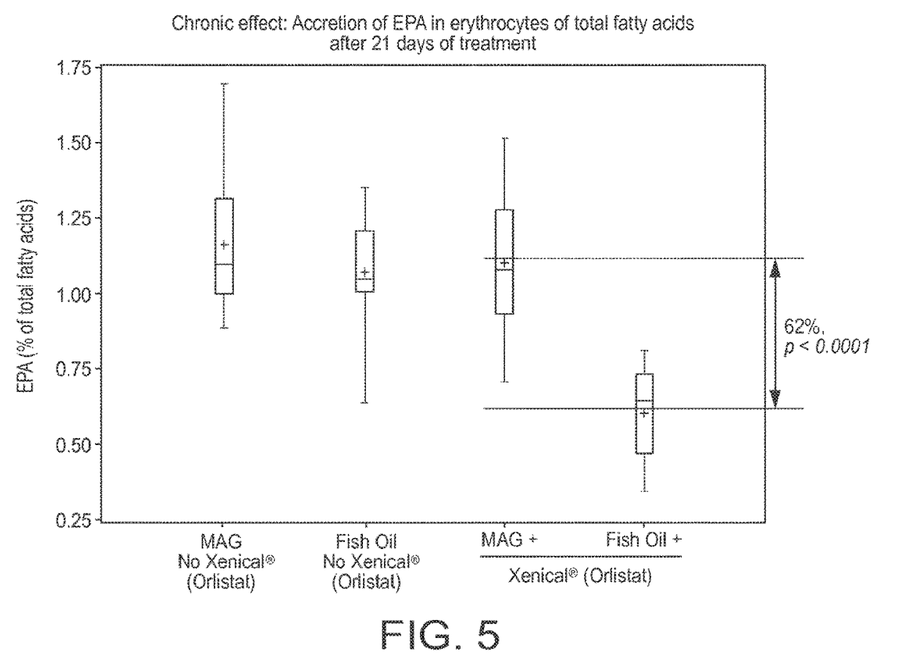
FIG. 5 shows chronic effects in the clinical study, namely accretion of EPA in erythrocytes as percentage of total fatty acids after 21 days of treatment.
Figure 6:
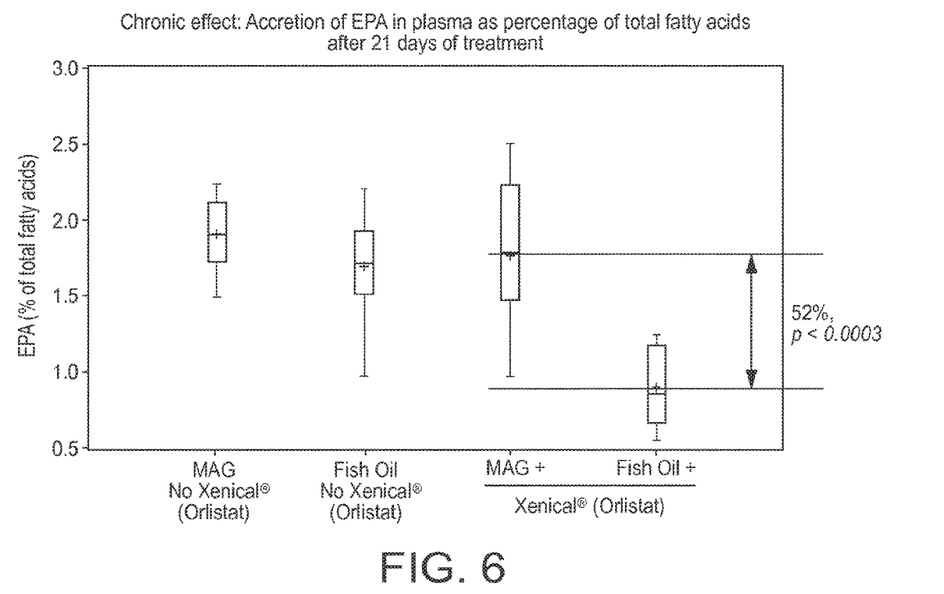
FIG. 6 shows chronic effects in the clinical study, namely accretion of plasma in erythrocytes as percentage of total fatty acids after 21 days of treatment.

The pharmacokinetic results (FIG. 4) show that the acute effect from treatment with sn-1(3) MAG and XENICAL® (ORLISTAT) is statistically significant relative to treatment with fish oil and XENICAL® (ORLISTAT) (p=0.0125). The accretion of EPA in erythrocytes after 21 days (FIG. 5) shows that the chronic effect of treatment with sn-1(3) MAG and XENICAL® (ORLISTAT) is statistically significant, especially in comparison to treatment with fish oil and XENICAL® (ORLISTAT) (p=0.0001). The accretion of EPA in plasma after 21 days (FIG. 6) shows that the chronic effect of treatment with sn-1(3) MAG and XENICAL® (ORLISTAT) is statistically significant relative to treatment with fish oil and XENICAL® (ORLISTAT) (p=0.0003).

This clinical trial confirmed that, in obese subjects treated with XENICAL® (ORLISTAT), sn-1(3) MAG is a better carrier for EPA than fish oil (TAG).

Example 3

In vitro digestion to assess lipidic components bioaccessibility. Simulated or in vitro digestion is a model to be used to assess the stability of lipidic components such as liposoluble vitamins and carotenoids during the digestive phases (oral, gastric and small intestinal) and the extent of partitioning of lipidic components into mixed bile salt micelle fraction (essential step for absorption of lipophiles). Partitioning of lipidic components into mixed bile salt micelle is also referred as "bioaccessibility" and expressed as efficiency of micellarization. In each step type of enzymes are adapted as needed (e.g. malabsorption vs. control) as well enzymes that are fit to purpose (e.g., TAG, MAG, vitamins, carotenoids).

In the procedure fish oil was used as a source of triacylglycerols (TAG). Monoacylglycerols (MAG) were purchased from Cognis GmbH, Germany and mixed with sunflower oil at the ratio of 1:0.8 (w/w).

Triacylglycerols and Monoacylglycerols mixed with β-carotene were assessed in vitro using a digestion model where digestive enzymes and bile salts were reduced to obtain mal-digestion and mal-absorption conditions.

To simulate gastric digestion, MAG or TAG plus β-carotene were incubated 10 min at 37 C, in order to have a homogeneous mixture. A solution of different salts (NaCl, CaCl2 and KCl) and 1% F-127 emulsifier were added. pH was adjusted to 2.5 before the addition of pepsin. The digestion solution was incubated 1 h at 37° C.

To mimic intestinal digestion, pH was adjusted to 6, bile extract, pancreatin and lipase solutions were added to the previous digestion solutions. pH was adjusted to 6.5 and the simulated digestions incubated for 2 h at 37° C.

After a liquid/liquid extraction, levels of β-carotene were measured by HPLC under the following analytical conditions: mobile phase: acetonitrile/terahydrofurane/methanol/1% ammonium acetate, flow rate: 1.5 mL/min. Detection: photodiode array and fluorometry.

The digestion of β-carotene was followed through the above mentioned in vitro digestion system to evaluate whether β-carotene digestion was more effective with MAG than with TAG.

Figure 8:
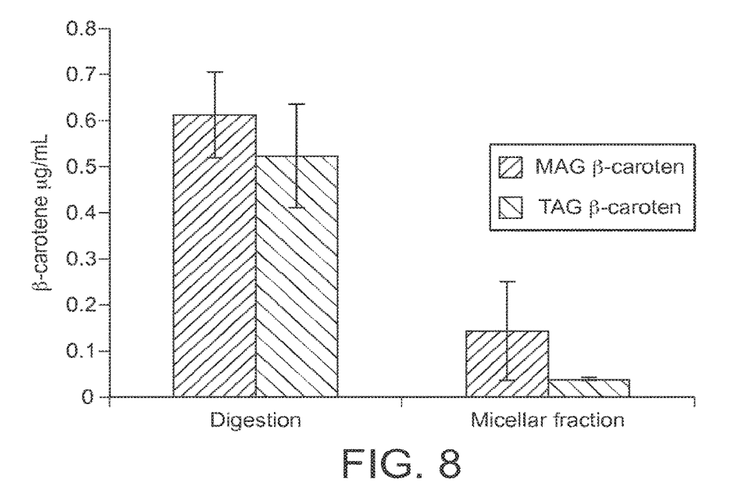
FIG. 8 shows the amount of β-carotene measured in the digestion solution and in the micellar fraction (on cells) in an in-vitro digestion model.

In the above described in vitro model for mal-digestion and mal-absorption conditions, it was observed that MAG has the tendency to improve digestion and micellization of β-carotene when compared to TAG (FIG. 8). From FIG. 8 is seen that the amount of β-carotene measured in the digestion solution and in the micellar fraction (on cells) is higher with MAG than TAG, indicating improved digestion and micellization of β-carotene.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of improving absorption of fat-soluble nutrients in an individual having a condition in which the absorption has been compromised, the condition is a low calorie diet in which 800 calories/day or less is consumed by the individual, the method comprising administering a fat-soluble nutrient and a therapeutically effective amount of monoacylglycerols to the individual.

2. The method of claim 1 wherein the monoacylglycerols are administered concurrently with the fat-soluble nutrient.

3. The method of claim 1 wherein the monoacylglycerols comprise a therapeutically effective amount of sn-1(3) monoacylglycerols.

4. The method of claim 1 wherein the amount of monoacylglycerols administered to the individual is therapeutically effective to enhance delivery of the fat-soluble nutrient in the individual.

5. The method of claim 1 wherein the monoacylglycerols comprise a functional fatty acid.

6. The method of claim 1 wherein the monoacylglycerols are selected from the group consisting of MAG-DHA, MAG-EPA and MAG-ARA.

7. The method of claim 1 comprising administering the fat-soluble nutrient and the monoacylglycerols to the individual daily for at least three weeks.

8. The method of claim 1 wherein the fat-soluble nutrient is selected from the group consisting of fat-soluble vitamins, carotenoids, and mixtures thereof.

9. The method of claim 1 wherein the fat-soluble nutrient is selected from the group consisting of vitamin A, isoforms of vitamin A, vitamin D, isoforms of vitamin D, vitamin E, isoforms of vitamin E, vitamin K, isoforms of vitamin K, beta-carotene, lutein, and mixtures thereof.

10. The method of claim 1 further comprising administering a lipase B inhibitor to the individual concurrently with the monoacylglycerols.

11. The method of claim 1 wherein no more than 25 wt. % of the monoacylglycerols are Sn-2 monoacylglycerols.

12. The method of claim 1 wherein no more than 15 wt. % of the monoacylglycerols are Sn-2 monoacylglycerols.

13. The method of claim 1 wherein the monoacylglycerols and the fat-soluble nutrient are administered in a composition in which the monoacylglycerols contribute 5% to 40% of the calorie content of the composition.

14. A method of improving absorption of fat-soluble nutrients in an individual having a having a condition in which the absorption has been compromised, the condition is a low fat diet in which 125 g of calories from fat/day or less is consumed by the individual, the method comprising administering a fat-soluble nutrient and a therapeutically effective amount of monoacylglycerols to the individual.

15. A method of improving absorption of fat-soluble nutrients in an individual having a condition in which the absorption has been compromised, the condition is selected from the group consisting of a diet low in fat, a diet low in calories, and a combination thereof, wherein the diet low in calories or the diet low in fat is a diet that solely uses liquid products restricting caloric intake while providing complete nutrition, the method comprising administering a fat-soluble nutrient and a therapeutically effective amount of monoacylglycerols to the individual.

16. The method of claim 15 wherein the monoacylglycerols are provided by one or more of the liquid products.

* * * * *